United States Patent
Scholz et al.

(10) Patent No.: US 7,888,659 B2
(45) Date of Patent: Feb. 15, 2011

(54) SPATIALLY-RESOLVED MEASUREMENT METHOD FOR THE DETECTION OF MELANIN IN FLUOROPHOR MIXTURES IN A SOLID SAMPLE

(75) Inventors: Matthias Scholz, Am Mellensee (DE); Dieter Leupold, Berlin (DE)

(73) Assignee: LTB Lasertechnik Berlin GmbH, Berlin (DE)

( * ) Notice: Subject to any disclaimer, the term of this patent is extended or adjusted under 35 U.S.C. 154(b) by 126 days.

(21) Appl. No.: 12/306,562

(22) PCT Filed: Jun. 17, 2007

(86) PCT No.: PCT/DE2007/001076

§ 371 (c)(1),
(2), (4) Date: Dec. 24, 2008

(87) PCT Pub. No.: WO2008/000223

PCT Pub. Date: Jan. 3, 2008

(65) Prior Publication Data

US 2009/0224172 A1     Sep. 10, 2009

(30) Foreign Application Priority Data

Jun. 28, 2006   (DE) ................. 10 2006 029 809

(51) Int. Cl.
    *G01N 21/64* (2006.01)
(52) U.S. Cl. .................................. 250/459.1
(58) Field of Classification Search ................ 600/476;
            250/459.1, 458.1, 461.1, 461.2
    See application file for complete search history.

(56) References Cited

U.S. PATENT DOCUMENTS 5,034,613 A   7/1991   Denk et al.

(Continued)

FOREIGN PATENT DOCUMENTS

DE       4414940        11/1995

(Continued)

OTHER PUBLICATIONS

Anikijenko et al., "In Vivo Detection of Small Subsurface Melanomas in Athymic Mice Using Noninvasivie Fiber Optic Confocal Imaging," 2001, The Journal of Investigative Dermatology, pp. 1442-1448.*

(Continued)

*Primary Examiner*—David P Porta
*Assistant Examiner*—Kiho Kim
(74) *Attorney, Agent, or Firm*—Leydig, Voit & Mayer, Ltd.

(57) ABSTRACT

A method of obtaining a spatially resolved measurement for the detection of melanin in fluorophore mixtures of a solid sample includes emitting at least one pulse of light from a laser light source onto the solid sample at an excitation wavelength between 300 nm and 1000 nm so as to provide fluorescence excitation of the melanin by photon absorption. The pulse of light has a photon flux density between $10^{26}$ to $10^{28}$ photons per $cm^2$ per second and a pulse length between 0.5 ns and 5 ns. An emitted spectral fluorescence response of the melanin is provided by evaluating a number of photons emitted at fluorescence wavelengths between 400 nm and 700 nm as to identify the melanin.

20 Claims, 6 Drawing Sheets
(5 of 6 Drawing Sheet(s) Filed in Color)

U.S. PATENT DOCUMENTS

| | | | | |
|---|---|---|---|---|
| 5,036,006 | A | * | 7/1991 | Sanford et al. .............. 435/459 |
| 5,555,885 | A | | 9/1996 | Chance |
| 6,007,996 | A | * | 12/1999 | McNamara et al. ............ 435/6 |
| 6,528,802 | B1 | | 3/2003 | Koenig et al. |
| 2004/0004194 | A1 | * | 1/2004 | Amblard et al. .......... 250/458.1 |
| 2004/0073119 | A1 | | 4/2004 | Mycek et al. |
| 2004/0124366 | A1 | * | 7/2004 | Zeng et al. ............... 250/458.1 |

FOREIGN PATENT DOCUMENTS

| | | |
|---|---|---|
| DE | 19719344 | 11/1998 |
| DE | 19935766 | 2/2001 |
| DE | 19939706 | 3/2001 |
| DE | 10065146 | 7/2002 |
| DE | 10239028 | 3/2003 |
| WO | WO-02069784 | 9/2002 |

OTHER PUBLICATIONS

Konig et al., "Optical Tomography of Human Skin with Subcellular Spatial and Picosecond Time Resolution using Intense Near Infrared Femtosecond Laser Pulses," 2002, Proceedings of SPIE, vol. 4620, pp. 191-201.*

Xu et al., "Identification and location of the pigment granules in the retinal pigment epithelium cells using fluorescence technology," 2006, IEEE International Symposium on Biophotonics, Nanophotonics, and Matamaterials pp. 68-71.*

Stephen P. Nighswander-Rempel et al. "A quantum yield map for synthetic eumelanin", The Journal of Chemical Physics 123, 2005, 194901, pp. 1-6.

Klaus Teuchner et al. "Femtosecond Two-photon Excited Fluorescence of Melanin", Photochemistry and Photobiology, 1999, vol. 70, No. 2, Aug. 2, 1999, pp. 146-151, XP009089146.

K. Hoffmann et at. "Selective Femtosecond Pulse-Excitation of Melanin Fluorescence in Tissue", J. Invest. Dermatol. 116, 2001, pp. 629-630.

Klaus Teuchner et al. "Fluorescence Studies of Melanin by Stepwise Two-Photon Femtosecond Laser Excitation" Journal of Fluorescence Kluwer Academic/Plenum Publishers USA, vol. 10, No. 3, Sep. 2000, pp. 275-281, XP002450035.

Anonym, "Selektive Melaninfluoreszenz informiert ueber Hautkrebs" [Selective melanin fluorescence informs about skin cancer], News from the LTB research, Jul. 21, 2006, Berlin, Germany, XP002450034.

International Search Report for International No. PCT/DE2007/001076, mailed on Oct. 2, 2007.

* cited by examiner

US 7,888,659 B2

SPATIALLY-RESOLVED MEASUREMENT METHOD FOR THE DETECTION OF MELANIN IN FLUOROPHOR MIXTURES IN A SOLID SAMPLE

CROSS-REFERENCE TO PRIOR APPLICATIONS

This application is a U.S. National Phase Application under 35 U.S.C. §371 of International Application No. PCT/DE2007/001076, filed on Jun. 17, 2007, and claims benefit to German Patent Application No. DE 10 2006 029 809.8, filed on Jun. 28, 2006. The International Application was published in German on Jan. 3, 2008 as WO 2008/000223 A1 under PCT Article 21(2).

FIELD

The present invention relates to a spatially resolved method for the detection of melanin in fluorophore mixtures in a solid sample by means of fluorescence excitation of the melanin present in the fluorophore mixture by means of photon absorption using at least one pulse of a laser light source and for the identification of the melanin present in the fluorophore mixture on the basis of its emitted spectral fluorescence response by evaluating the numbers of emitted photons.

BACKGROUND

Fluorescence examinations for the identification of specific substances have been known for a long time. The ability to emit light after photon absorption, i.e. to luminesce, is substance-specific. This is the basis of conventional luminescence analysis. Several million luminescent, i.e. fluorescing and/or phosphorescing organic compounds are known today, and it is often the case that several luminescent substances are present in a material that is to be examined. This often applies, for example, to measured samples and to issues encountered in biosciences and medicine. For example, human skin tissue contains at least ten different endogenous fluorophores, along with exogenous fluorophores, and consequently the autofluorescence spectrum of the skin is the result of many individual fluorescence bands. A number of methods are known, which generally have to be used in combination in order to yield a component analysis with fluorophore mixtures, for example, by varying the excitation wavelength, by turning to excitation spectra as a function of the fluorescence wavelengths, fluorescence decay behavior and polarization spectra, although employing combined methods is not only time-consuming but, for example, in cases where the fluorophore mixture is present in a matrix, might only be useable to a limited extent due to the optical properties of the matrix itself, such as self-absorption and scattering. Another complication of the analysis of fluorophore mixtures in matrices arises if the latter are non-homogeneous in terms of their optical properties and if the composition of the fluorophore mixture in these non-homogeneous matrices is additionally itself a function of the location. Such a situation exists in the matrix of human skin tissue, in view of the mixture of endogenous and exogenous fluorophores that is present there. The fluorophore component analysis with this matrix is also made more difficult in that it has a penetration depth for visible light that decreases sharply from the long-wave to the short-wave range. This drawback can be countered by non-linear fluorophore excitation by means of simultaneous two-photon absorption in the long-wave spectral range, but this considerably limits not only the above-mentioned broad combination of methods for the fluorophore component analysis and makes it extremely complicated, but above all, it also calls for the use of ultra-short, intense high-repeating laser light pulses in the femtosecond range (fs). This entails the well-known risk of photochemical bleaching of the fluorophores and, especially with in-vivo applications, there is also a risk of affecting the cell division rate caused by the requisite high photon flux densities of typically $\geq 10^{29}$ photons per $cm^2$ and per second, and by the high-repeating radiation regime.

However, it is precisely the fluorophore component analysis in human tissue that is of considerable interest, e.g. in conjunction with medical-diagnostic, pharmaceutical and cosmetic issues. In particular, the focus of attention is directed at the endogenous fluorophore melanin. Melanin occurs, among other places, in the skin, hair and eyes; it is responsible, for example, for skin and hair color, and it especially plays a central role, on the one hand, as a "sunscreen" and, on the other hand, in the degeneration of skin tissue into malignant melanoma, the black skin cancer. According to S. P. Nighswander-Rempel et. al. in "A quantum yield map for synthetic eumelanin" in J. Chem. Phys. 123, 2005, 194901-1-6, when it comes to fluorescence analysis, melanin has the serious drawback of an extremely small fluorescence quantum yield in the order of magnitude of $10^{-4}$ at the maximum; even a specific fluorescence quantum yield derived from the unusual absorption of melanin is only in the order of magnitude of $10^{-6}$. The absorption spectrum of melanin differs from that of almost all other organic fluorophores. Whereas the latter exhibit only individual discrete absorption bands between the near ultraviolet and the near infrared spectral ranges, melanin exhibits a monotonously decreasing absorption curve in the cited spectral range. Thus, when two-photon absorption in the red or near infrared spectral range is applied to fluorophore mixtures containing melanin, the results do not even come close to achieving a selective excitation of the melanin spectrally because every light wavelength that excites any fluorophore also excites melanin. German patent specification DE 199 39 706 C2 discloses that an accumulation of the excited melanin in comparison to all other fluorophores can be achieved by two-photon excitation with femtosecond pulses, meaning that, so to speak, a certain compensation for the low fluorescence quantum yield is possible. This is based on the fact that two-photon excitation of melanin takes place as a stepwise process of two consecutive one-photon absorptions via a real intermediate level (see K. Teuchner et. al. in "Femtosecond Two-photon Excited Fluorescence of Melanin" in Photochem. Photobiol. 70(2), 1999, pp. 146-151), in contrast to the usual simultaneous two-photon excitation with an only virtual intermediate level in the case of the other relevant fluorophores. However, the fluorescence-spectroscopic significance and analytical usefulness of this accumulation of excited melanin are limited by its extremely low fluorescence quantum yield in comparison to the other relevant fluorophores. It is known from the publication by K. Hoffmann et. al. "Selective Femtosecond Pulse-Excitation of Melanin Fluorescence in Tissue" in J. Invest. Dermatol. 116 (2001), 629-630 that, with this two-photon excitation based on femtosecond pulses, a red shift of the fluorescence can be measured in malignant melanoma ex-vivo in comparison to healthy skin tissue and a shortening of the fluorescence decay occurs (also see German patent application DE 102 39 028 B4).

U.S. Pat. No. 5,034,613 describes a laser microscope with a simultaneous two-photon fluorescence excitation that, in order to examine cell material, uses excitation wavelengths in the range from red to near infrared, i.e. between 640 nm and 1200 nm, with pulse lengths in the sub-picosecond range, i.e. $<10^{-12}$ seconds, here at 100 femtoseconds (fs), at a repetition rate of 80 MHz. A very high local light intensity arises due to the focusing at 1 µm. This very narrow focusing is meant to limit the bleaching of the fluorophores to the immediate observation area. Moreover, the two-photon excitation is supposed to suppress the so-called background fluorescence to a greater extent. German patent specification DE 44 14 940 C2 describes a luminescence scanning microscope using two-photon excitation that works with laser pulses that are greater than 1 picosecond (ps) in order to avoid the use of expensive femtosecond lasers. With an eye towards offsetting the low pulse power that is used so as to treat the examination objects gently, a greater measuring duration, i.e. a longer pulse sequence is used for the luminescence excitation. German patent application DE 197 19 344 A1 discloses an arrangement for the optical micromanipulation, analysis and processing of objects, said arrangement working with a wavelength spectrum for the excitation in the range between 400 nm and 1200 nm and pulse lengths in the nanosecond, picosecond and femtosecond ranges. The arrangement relates mainly to the use of a laser that can be tuned over the entire spectral range and less to the fluorescence excitation intended for the actual substance analysis. Nevertheless, this publication explicitly points out that only the pulse durations in the femtosecond range are used for the analysis. Pulse lengths in the range of picoseconds or longer are used exclusively for the micromanipulation.

German patent application DE 199 35 766 A1 describes a method for the optical excitation of fluorophore-marked DNA and RNA in which a simultaneous non-resonant multi-photon fluorescence excitation is used preferably at wavelengths in the range between 760 nm and 820 nm, and with power densities between 100 MW/cm$^2$ und 10 TW/cm$^2$. It is noted that the simultaneous two-photon or three-photon excitation is not known yet in the DNA/RNA analysis under discussion here. An example is presented in which various fluorophores with a wavelength of 770 nm, a pulse duration of 200 fs, a pulse frequency of 76 MHz and a power density of 500 GW/cm$^2$ could be excited to a high-contrast fluorescence spectrum with maxima between 480 nm and 650 nm. German patent specification DE 199 39 706 C2 describes the selection of fluorophores for substance marking in multi-photon laser scanning microscopy, comprising a stepwise resonant absorption with real intermediate levels. Here, a much lower laser intensity, i.e. photon flux density, is said to be necessary for the excitation, so that, on the one hand, less equipment is needed and, on the other hand, the risk of electric disruptive discharges and the photochemical effect of bleaching of the substance sample can be minimized after the one-photon absorption. In particular, mention is made of synthetic melanin as such a fluorophore in which the mechanism of action of the stepwise resonant multi-photon absorption is systematically utilized, i.e. the excitation is not achieved via virtual but rather via real intermediate levels. Concretely speaking, a wavelength of 800 nm, a pulse duration of 120 fs and a pulse energy of 1 µJ are used for the fluorescence excitation. The emitted fluorescence is in the blue-green-red spectral range at a maximum of 610 nm. German patent application DE 100 65 146 A1 describes a method and an arrangement for non-invasive three-dimensional optical examination and treatment of the skin that, for the multi-photon excitation of the body's own fluorophores, use pulsed laser radiation in the near infrared range at wavelengths of 700 nm to 1200 nm as well as pulse lengths of less than 20 ps with light intensities in the order of magnitude between gigawatts per cm$^2$ and terawatts per cm$^2$ at a pulse sequence frequency of 80 MHz. In particular, it is said that melanoma of the skin can be located and irreversibly damaged. It is described that resonant and non-resonant multi-photon fluorescence excitation of specific endogenous fluorophores, especially melanin, occurs, as a result of which it is said to be possible to distinguish between certain pathological tissue and healthy tissue on the basis of the ascertained arrangement of the fluorescence intensity and of the fluorescence lifetime. The exact mechanisms of action of the multi-photon excitation in conjunction with the excitation parameters as well as the interpretation of the fluorescence response for purposes of precisely locating pathological tissue are not discussed.

International patent publication WO 02/069784 describes a portable fluorescence lifetime spectrometer (FLS) for the simultaneous in-vivo analysis of the spectral and temporal fluorescence properties of tissue or cells in terms of their carcinogenic or pre-carcinogenic tissue components. The time-dependent fluorescence response of endogenous fluorophores such as collagen, elastin, NADPH and tryptophan is highly dependent on the biochemical environment and on its pH value and oxygen content, as a result of which a conclusion can be drawn as to whether the tissue is said to be healthy or diseased. In less than one second, the FLS can process the data about the transient decay behavior of a certain frequency band of the fluorescence of the examined tissue over periods of time averaging 360 picoseconds and consequently, it is suitable for in-vivo use. This publication does not present a new measuring method but rather a measuring device that has been optimized for a specific purpose.

German patent application DE 102 39 028 B4 describes a method for identifying naturally occurring or synthetically produced types of melanin. The occurring melanin is selectively excited—relative to other fluorophores present in the sample—by one-photon excitation and by stepwise, resonant two-photon excitation with laser pulses having a wavelength of 800 nm and at a pulse length in the femtosecond range, and the fluorescence spectrum obtained as the response to this is evaluated after spectral distribution and after being temporally resolved. On the basis of the spectral distribution of the obtained fluorescence intensities and of the decay behavior, it becomes possible to selectively distinguish among the various types of melanin and thus to draw a conclusion about the presence of tissue that is suspected of having a malignant melanoma.

In the state of the art, fluorophores in general and melanin in particular are regularly detected with laser pulses having pulse lengths in the femtosecond range, but at the most of less than 20 ps. The wavelength range is specified as being from 700 nm to 1200 nm, a wavelength of 800 nm being commonly used. The high-energy pulses are radiated highly repetitively at frequencies of, for example, 80 MHz, and they generate photon flux power densities that lie between 100 GW/cm$^2$ and several TW/cm$^2$.

SUMMARY

In addition to the above-mentioned local bleaching effects with still-unknown subsequent reactions and in addition to the risk of affecting the cell division rate at pulse power densities of more than 100 GW/cm$^2$, there is yet another source of danger stemming from non-linear fluorophore excitation in-vivo using intense, ultrashort light pulses, which has been almost completely ignored up until now: the dangerously high effect of an undesired three-photon excitation of fluorophores that results from a one-photon absorption from the excitation state that follows the simultaneous two-photon absorption. In the literature, a three-photon absorption that is possible in the case of non-linear fluorophore excitation has only been rarely mentioned, and then, it was incorrectly interpreted as a simultaneous three-photon absorption because, due to its extremely small effective cross section, it was said to have an infinitesimally small effect. Owing to this misinterpretation, the concrete risk that stems from the actual occurrence of two-photon absorption with subsequent one-photon absorption is not recognized. Energetically, this process corresponds to an excitation in the UV-B or even UV-C range. Such a high carcinogenic potential makes the use of the method of non-linear fluorophore excitation with femtosecond pulses in human tissue very risky and increases, for example, the risk of DNA protein cross-links. In view of the described effects, this form of melanoma diagnosis on the basis of femtosecond pulses appears to be too risky for in-vivo applications.

Pulse lengths in the femtosecond range call for more complex equipment, making it impossible to use handy and easily operable devices, for example, for melanoma diagnosis. If the benefit of selective melanin detection does not outweigh the drawbacks and risks described above, then the diagnostic methods aimed at in-vivo use have to operate at power densities well below 100 $GW/cm^2$, the threshold for cell damage. The latest findings on the risk of an actual three-photon absorption with carcinogenic UV-C potential that occurs unnoticed instead of what was assumed to be a two-photon absorption call for a markedly more stringent stipulation of power densities $\leq 1$ $GW/cm^2$. The high energy input into the tissue matrix, caused by the measured systems based on high-repeating laser systems, should be avoided if the fluorophore mixtures to be examined contain melanin, since practically all of the energy absorbed in the melanin remains in the tissue and is necessarily converted, for example, into heat or into photochemical subsequent processes. This is an aspect of the extremely low fluorescence quantum yield of melanin. Other fluorophores typically release most of the absorbed excitation energy in the form of fluorescence radiation.

An aspect of the present invention is thus to provide a spatially resolved method for the detection of melanin in fluorophore mixtures in a solid sample in such a way as to minimize or avoid one or more of the drawbacks having to do with complex equipment, complicated handling, multi-step methods and ambiguous detection results. It is another alternative aspect of the present invention to minimize or avoid risks associated with high irradiation intensities that trigger bleaching, affect cell division mechanisms, cause burns and can be carcinogenetic in in-vivo detection procedures.

In an embodiment, the present invention provides a method of obtaining a spatially resolved measurement for the detection of melanin in fluorophore mixtures of a solid sample wherein at least one pulse of light is emitted from a laser light source onto the solid sample at an excitation wavelength between 300 nm and 1000 nm so as to provide fluorescence excitation of the melanin by photon absorption. The pulse of light has a photon flux density between $10^{26}$ to $10^{28}$ photons per $cm^2$ per second, a pulse length between 0.5 ns and 5 ns. An emitted spectral fluorescence response of the melanin is provided by evaluating a number of photons emitted at fluorescence wavelengths between 400 nm and 700 nm so as to identify the melanin.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The spatially resolved measuring method according to the invention for the detection of melanin in fluorophore mixtures in a solid sample is described in greater detail below with reference to the schematic figures. The following is shown.

Figure 1A:
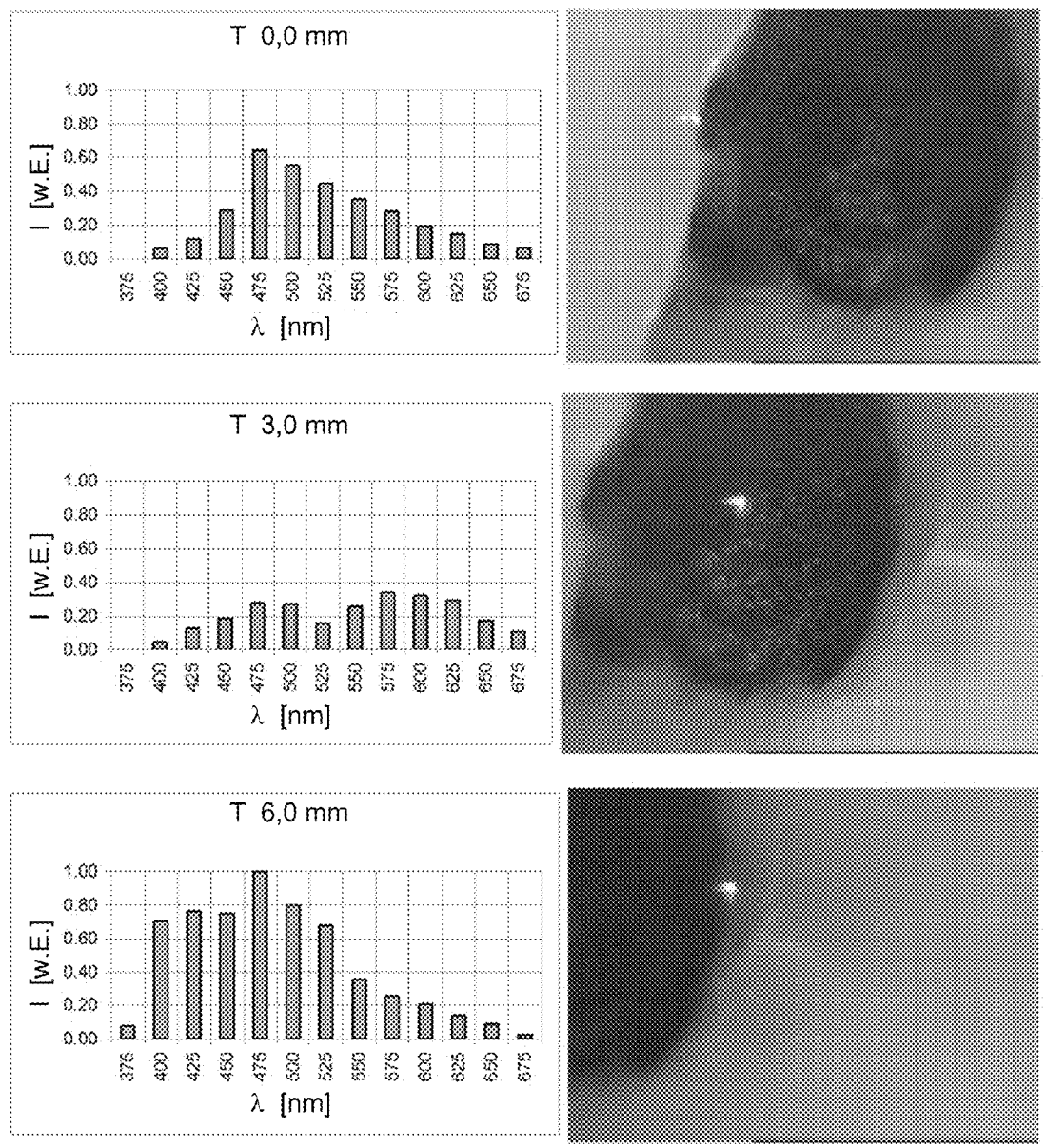
FIG. 1A fluorescence spectra of a melanoma, taken with excitation pulses at 810 nm and 2 ns; with photographs of the measurement sites, FIG. 1B fluorescence spectra of a melanoma, taken with excitation pulses at 880 nm and 2 ns; with photographs of the measurement sites, FIG. 2 comparison of two fluorescence spectra of a melanoma and of healthy skin, taken with excitation pulses at 810 nm and 0.7 ns, FIG. 3A photograph of a skin region with a malignant melanoma, FIG. 3B grayscale overview photograph of the skin region mentioned under 3A in the light of the fluorescence generated with 337 nm-excitation pulses, FIG. 3C fluorescence spectra at the measurement sites shown in the photograph of FIG. 3B at 810 nm and 2 ns two-photon excitation pulses, FIG. 4A arrangement for taking images in the light of the fluorescence using two-photon excitation, and FIG. 4B measuring arrangement for fluorescence spectra using two-photon excitation.

The spatially resolved method according to an embodiment of the present invention for the detection of melanin in fluorophore mixtures in a solid sample is provided for through fluorescence excitation of the melanin only which is present in the fluorescence mixture by photon absorption with at least one pulse of a laser light source that, at a pulse length of 0.5 ns to 5 ns, generates an excitation wavelength in the range between 300 nm and 1000 nm having a photon flux density of $10^{26}$ to $10^{28}$ photons per $cm^2$ and per second. The detection is made by counting the photons irradiated in the fluorescence spectrum between 400 nm and 700 nm.

In a particularly surprising manner, it has been found that, in contrast to the current knowledge according to the literature (K. Teuchner et al. J. Fluor. 10/3, 2000, 275-281 J. Fluor. 10/3, pp. 275-281, 2000), the fluorescence spectrum of melanin caused by two-photon excitation can also be excited with laser pulses having pulse lengths of more than about 100 fs, e.g., with pulses in the nanosecond range; preferably, this is done at a pulse duration of 2 ns. The present invention offers significant advantages which can be demonstrated theoretically and practically on the basis of the fact that the occupation density of the fluorescence level occupied by means of two-photon absorption is dependent on the pulse duration. A prolongation of the pulse duration by 4 orders of magnitude (e.g., 100 fs to 1 ns)—with otherwise unchanged parameters in the simultaneous two-photon absorption for the usual fluorophores—likewise raises the occupation density in the fluorescence level by 4 orders of magnitude, whereas for stepwise two-photon absorption in melanin, it raises the occupation density by 8 orders of magnitude. Since this occupation density is dependent by a square function on the excitation intensity for both types of two-stage absorption, the laser pump intensity of the pulses in the nanosecond range could theoretically be reduced by 4 orders of magnitude in comparison to the pulses of about 100 fs in order to obtain the same fluorescence intensity for melanin for excitation in the nanosecond range as is obtained in the method with pulses of about 100 fs. In contrast, the fluorescence of the other usual fluorophores would have been reduced by 4 orders of magnitude, i.e. it would be relatively unmeasurable. This is approximately confirmed in actual practice as well. In order to obtain a clear selective fluorescence response of the melanin with the same detection system in case of excitation in the nanosecond range, the photon flux density can be reduced by almost 3 orders of magnitude in comparison to the excitation by about 100 fs and, in an embodiment of the method according to the present invention, can lie at $10^{27}$ photons per $cm^2$ and per second, corresponding to approximately 300 $MW/cm^2$ for photons of the red to near infrared spectral range. At this excitation and under identical detection conditions, the other usual fluorophores are unmeasurably weak, i.e. a reliable selective detection of the melanin fluorescence from the fluorophore mixture on hand is achieved. In this process, at the same time, the requisite laser intensities have been reduced by several orders of magnitude, i.e. the risk of the above-mentioned radiation damage is drastically diminished. In order to detect the melanin fluorescence, according to other embodiments of the method according to the invention, averaging over an accumulation number of 2 to 100 individual pulses of the laser light source can be carried out with low energy input and the spectral fluorescence response can be ascertained in wavelength increments of about 25 nm.

According to other embodiments of the method according to the present invention, the fluorescence excitation can be carried out by excitation wavelengths in the range between 300 nm and 350 nm exclusively by one-photon absorption and the fluorescence response can be ascertained over the entire solid sample in the form of a visual depiction. Preferably, the excitation wavelength can be 337 nm and the visual depiction can be made by direct optical photography of the fluorescence emitted in the visible range. It has surprisingly been found that skin tissue regions with malignant melanoma have a characteristic structuring in the intensity distribution of the fluorescence image of the entire region if this image is generated with one-photon excitation and is created with a highly sensitive, gated detection system. For this purpose, excitations with a nanosecond pulse nitrogen laser (337 nm) and spectrally selected fluorescence within the range from 400 nm to 650 nm are suitable. It has also surprisingly been found that such a reduction of the fluorescence of the fluorophores that are usually dominant in case of conventional one-photon excitation occurs in malignant melanoma, and also that, at excitation and detection wavelengths selected according to the embodiments of the method, this fluorescence extinction can be used as a first indication of a malignant degeneration. Therefore, with an embodiment of the method according to the present invention, the spatially resolved detection of skin tissue regions of interest can be carried out in the fluorescence light of spectrally filtered fluorophores excited by suitable UV-photons from nanosecond pulses in order to recognize regions that are suspected of having a malignant melanoma.

According to further embodiments of the method according to the present invention, the fluorescence excitation can be effectuated by excitation wavelengths in the range between 600 nm and 1000 nm exclusively by stepwise two-photon absorption and the fluorescence response can be ascertained locally and selectively at the fluorescence wavelength of or near 475 nm that is characteristic for the melanin type eumelanin, and at the fluorescence wavelength of or near 575 nm that is characteristic for the melanin type pheomelanin. Preferably, the excitation wavelength can be between 800 nm and 900 nm and the local spatial resolution can lie at measuring spots in the range between 40 μm and 100 μm. In order to further minimize risk during in-vivo fluorescence measurements, the excitation wavelength can be shifted from the otherwise normally employed 800 nm to wavelengths of about 900 nm. In this manner, the prescribed laser wavelength already precludes that the critical UV range below 300 nm for non-linear three-photon absorption will be reached. The energy of 3 hv for $\lambda=c/v=900$ nm corresponds to a wavelength of 300 nm. This energetically essential shift of the excitation wavelength for melanin to the range of about 900 nm is described here for the first time and used according to the invention. It has also surprisingly been found that melanin can also still be excited at a wavelength of about 900 nm to yield a measurable stepwise excited fluorescence. Such a melanin fluorescence, for example, in human skin tissue in a paraffin section ex-vivo, exhibits a spectrally wide, asymmetrical profile with a maximum in the blue-green spectral range at about 475 nm and a gradually tapering flank into the red spectral range, implicitly depicting a second component. It has also surprisingly been found that, in case of degeneration of the skin tissue into a malignant melanoma, the spectral profile of the melanin fluorescence changes significantly. It now clearly exhibits two bands, in the paraffin section at 475 nm and 575 nm, i.e. the yellow-red spectral fraction of the fluorescence is much more pronounced. This situation stems from the significant decrease in the total fluorescence of the melanin in the malignant melanoma as compared to healthy tissue, and this decrease comes at the expense of the shortwave component. These pure fluorescence spectra of melanin, which were obtained for the first time through the selection of the process parameters according to an embodiment of the present invention, make it clear during the excitation of the fluorophore mixture in the skin tissue that all of the fluorescence spectra of skin tissue that were previously measured exclusively with pulses in the femtosecond range do not reflect a pure melanin fluorescence but rather also fractions of fluorophores with simultaneous two-photon absorption. This can be seen explicitly in the fluorescence detection of skin tissue with a malignant melanoma in paraffin, in which one and the same tissue region was excited with 800 nm pulses in the femtosecond range as well as with pulses in the nanosecond range. The minimum that occurs at 525 nm during the fluorescence excitation in the nanosecond range is concealed by the FAD fluorescence (flavin adenine dinucleotide). Hence, the method according to an embodiment of the present invention provides greater detection sensitivity to melanin fluorescence in the skin tissue caused by pathological changes. This detection sensitivity benefits the recognition of the onset of malignant degeneration in nevi and it provides other advantages for malignant degenerations, along with the advantage of non-invasiveness, such as the elimination of the various above-mentioned risks of radiation load as well as the advantage of the much simpler equipment requirements for pulses in the nanosecond range in comparison to pulses in the femtosecond range.

In another embodiment of the method according to the present invention, both versions of the method described above are combined. For this purpose, the fluorescence detection of skin regions that are to be examined in their entirety is carried out in the light of a fluorescence that is excited by one-photon absorption and the selection of sample regions of special interest is made by ascertaining fluorescence extinctions in the fluorescence response. Subsequently, in these selected regions, a fluorescence response excited by means of the stepwise two-photon absorption is ascertained locally and selectively, and the occurring fraction especially of the melanin type pheomelanin is ascertained by determining the appertaining number of emitted photons. The extent of the fluorescence extinction to be determined in the first part of the method can advantageously be ascertained on the basis of the color or grayscale gradations that occur in the visual depiction proportionally to said fluorescence extinction, whereby the darkest regions with the greatest fluorescence extinction are selected for further examination in the second part of the method. The ratio of the occurring fractions of the melanin types eumelanin and pheomelanin can also be ascertained. Moreover, the method can be used for solid samples of tissue parts of the human skin, of the human fundus of the eye or of human hair, whereby the method can be carried out either ex-vivo in solid samples stabilized in paraffin and fixed in formalin, or else in-vivo in solid samples fixed in their natural environment. Preferably, the spatially resolved measuring method for the detection of melanin in fluorophore mixtures in a solid sample can be used for the technical objective of early detection of malignant melanomas in human skin tissue as a solid sample.

All of the numerical values and diagrams showing fluorescence spectra indicated in the figures described below refer to spectrally uncorrected fluorescence spectra that were obtained under comparable test conditions using the measuring arrangements shown in FIG. 4.

Figure 1B:
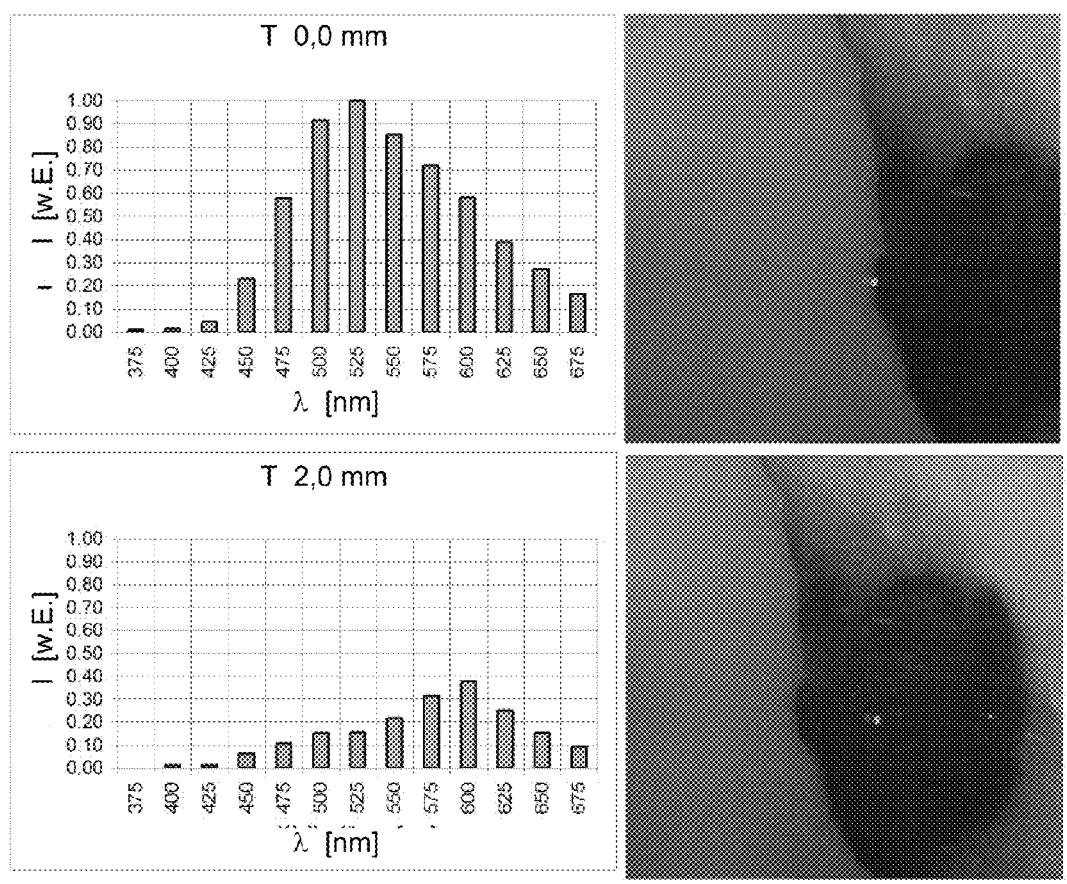

FIG. 1A shows three fluorescence spectra of a malignant melanoma using two-photon excitation and excitation pulses at a wavelength of 810 nm and at a pulse length of 2 ns, with photographs of the measurement sites. The photographs on the right-hand side show a section made perpendicular to the skin surface through a malignant melanoma that is 7.7 mm thick and that is embedded in paraffin. The light-colored spot in it shows the specific measurement site at a measuring depth of 0 mm at the top, 3 mm in the middle and 6 mm at the bottom. The fluorescence spectra obtained with the above-mentioned parameters are shown on the left-hand side. The measuring device is set in such a way that each measuring region has a diameter of 70 µm. The fluorescence spectra at the top and bottom, directly on the skin surface and directly at the lower end of the malignant melanoma show the spectrum of healthy skin tissue with the characteristic form of eumelanin at 475 nm. The fluorescence spectrum in the middle, in the center of the malignant melanoma shows the relative form of the fraction that is characteristic of pheomelanin, i.e. of the malignant melanoma, at 575 nm and the gap at 525 nm as evidence of the suppression of the flavin fluorescence as well as the decrease in the intensity of the total fluorescence in the malignant melanoma. FIG. 1B shows two examples of fluorescence spectra of a malignant melanoma using two-photon excitation and excitation pulses at a wavelength that is shifted to 880 nm and at a pulse length of 2 ns, with photographs of the measurement sites at a measuring depth of 0 mm at the top and 2 mm at the bottom, and having a diameter of 70 µm. The ascertained fluorescence spectra are shown again on the left-hand side. The measured results demonstrate that the malignant melanoma can also be reliably identified even when the excitation is at a wavelength close to 900 nm, with the decisive advantage of a risk-free measurement, especially for in-vivo applications, since even three-photon absorption, which has a negligible probability under the present measuring conditions anyway, does not lead to the UV-C range. As a result of the low-energy excitation that results from the lengthening of the excitation wavelength, the autofluorescence spectrum is altogether shifted somewhat bathochromically, the characteristic maxima are shifted from 475 nm to 525 nm, or from 574 nm to 600 nm. The fluorescence spectrum at the top again shows the spectrum of healthy skin tissue with the bathochromically shifted form of eumelanin at 525 nm. The fluorescence spectrum at the bottom again shows the spectrum for the malignant melanoma with the bathochromically shifted form of pheomelanin at 600 nm as well as once again the decrease in the intensity of the total fluorescence in the malignant melanoma.

Figure 2:
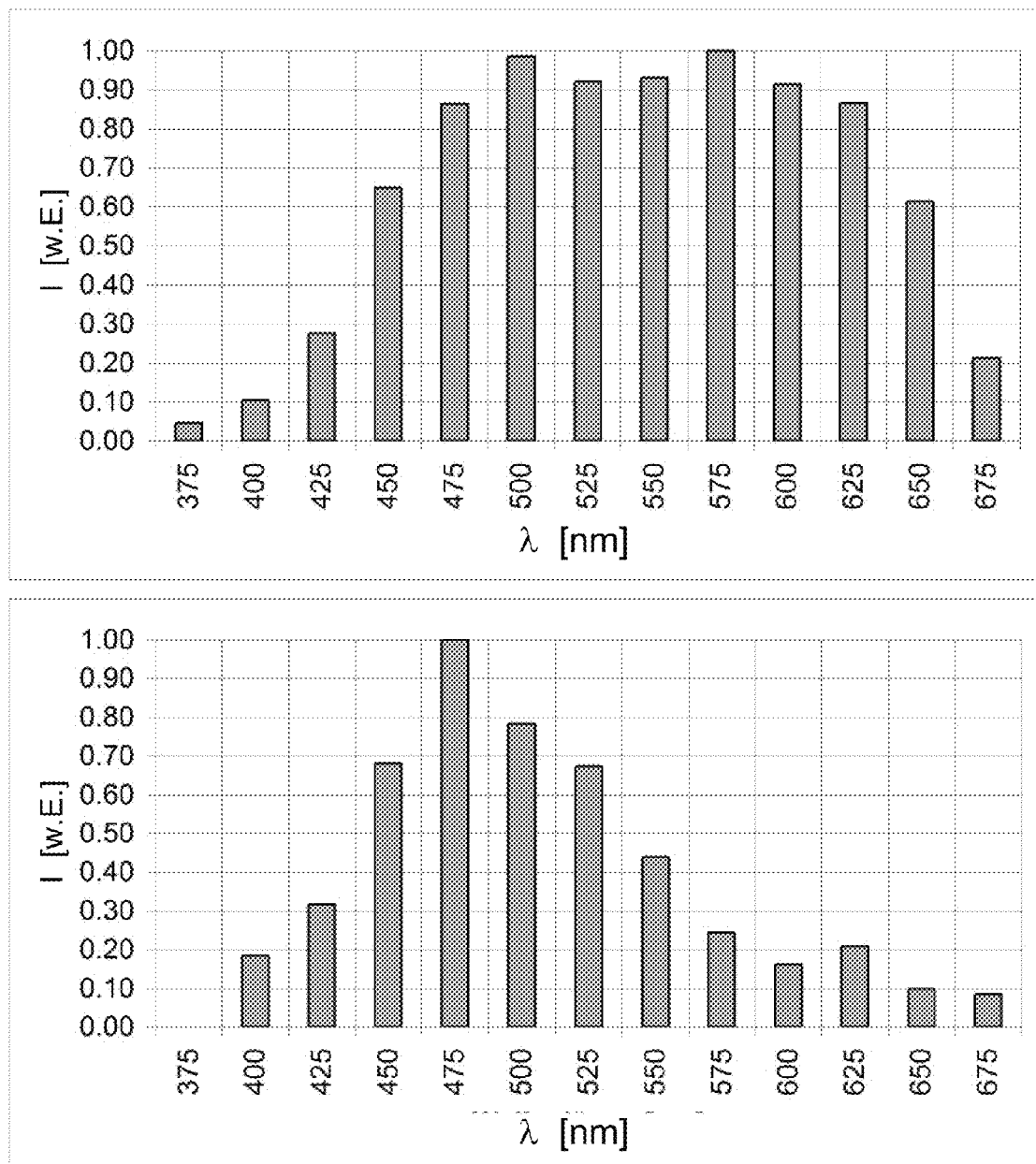

FIG. 2 compares the fluorescence spectra of skin tissue with a malignant melanoma and of healthy skin tissue. The excitation parameters are: two-photon excitation at a wavelength of 810 nm and at a pulse duration of 0.7 ns, with a diameter of the measurement site of 70 µm. The samples stem from several measuring procedures and consequently, the two fluorescence spectra are only qualitatively but not quantitatively comparable. The lower fluorescence spectrum stems from a sample of healthy skin and shows the characteristic spectral distribution of the fluorescence with a clear focal point at 475 nm for eumelanin. The upper fluorescence spectrum stems from a sample with a malignant melanoma and shows a clear increase in the fluorescence at 575 nm for pheomelanin, the indicator of the malignant melanoma, and the characteristic gap at 525 nm for the flavin fluorescence suppression. In this example, the reduction in the total fluorescence that occurs in such cases is not visible, since the two fluorescence spectra cannot be standardized with respect to each other because they stem from different measuring procedures. For example, the thicknesses of the paraffin layers over the skin samples that are to be overcome can differ. Irrespective of that, the resulting fluorescence spectra of the two samples of qualitatively clearly diseased and healthy skin tissue can be identified and they show that, already on the basis of the spectral effect, a clear-cut conclusion can be drawn about the condition of the sample at the measurement site, even with detections using completely different conditions while the same pulse parameters for the fluorescence excitation are retained.

Figure 3A:
Figure 3B:
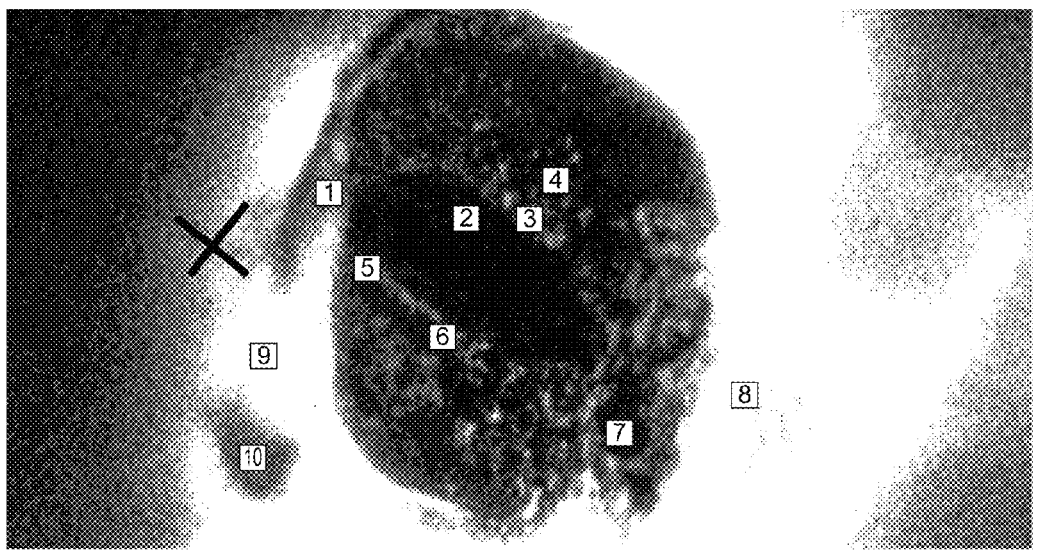
Figure 3C:
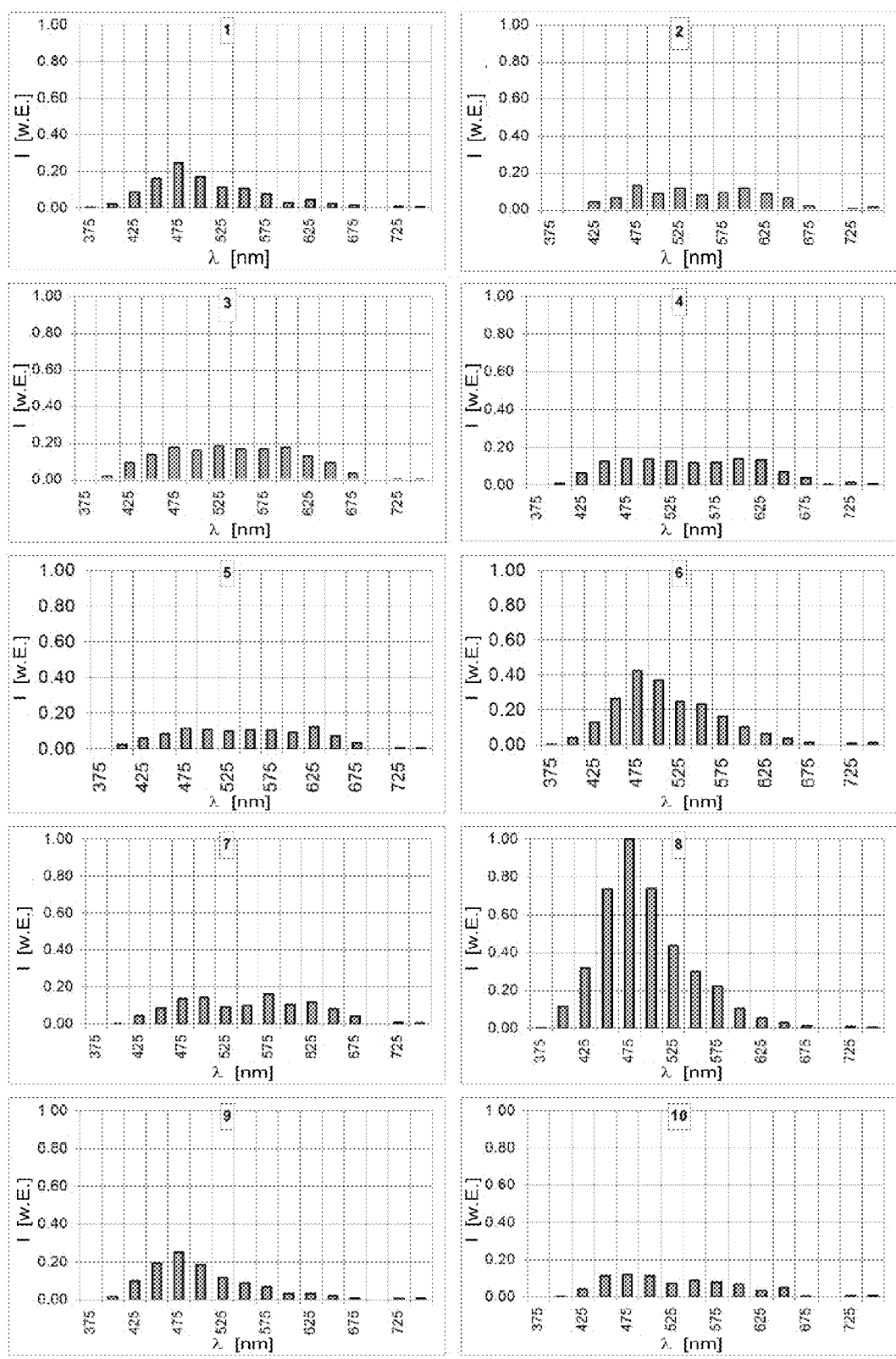

FIG. 3A shows a photograph of a skin tissue region with a malignant melanoma under normal light and embedded in paraffin as shown in FIG. 1. The cross identifies a striking point on the skin surface of the sample. For purposes of a size comparison, the distance from the cross to the light spot is 3 mm. In order to make an assessment of suspicious regions, FIG. 3B shows a grayscale image as an overview of the same measured object as in FIG. 3A, here in the light of fluorescence excited at 337 nm. For purposes of making a comparison with FIG. 3A, the cross is entered at the identical place. Ten measurement sites are marked whose fluorescence spectra are also shown below in FIG. 3C. The dark region that is suspected of having a malignant melanoma is especially clearly visible around the measurement site 2. The fluorescence spectra at the ten measurement sites were excited with pulses at a wavelength of 810 nm and at a pulse duration of 0.7 ns. Each fluorescing region has a diameter of 70 µm. The ordinate of the spectra is standardized for the maximum of the entire measurement series, i.e. in addition to the spectral variation, the intensity variation over the measurement sites is also visible. The measurement site 8 located outside of the suspicious region that can be seen in the overview image, especially at measurement site 2, also proves to be quite unsuspicious in the spectral analysis and, with its undisturbed fluorescence typical of healthy skin tissue, serves as a standardization reference for all of the other nine fluorescence spectra in this figure. At the measurement site 9, the undisturbed spectral distribution typical of healthy skin tissue is still detected with the practically continuous course of the measured value decrease between 475 nm and 675 nm, but with a marked weakening of the total fluorescence, as a result of which a fundamental suspicion of an irregularity exists, but not of a skin region affected by a malignant melanoma in the early stage. The measurement sites 1 and 6 show a small but clearly recognizable deviation from this continuous course, in each case at 550 nm, and consequently, they give rise to a greater suspicion that the appertaining skin region is affected with a malignant melanoma at an early stage. The fluorescence spectra at the other measurement sites 2, 3, 4, 5, 7 and 10 show the forms of the spectral distribution with maxima around 575 nm that are typical for disease with a malignant melanoma, and also show the characteristic gap around 525 nm for the flavin fluorescence suppression as well as the marked weakening of the total fluorescence.

Figure 4A:
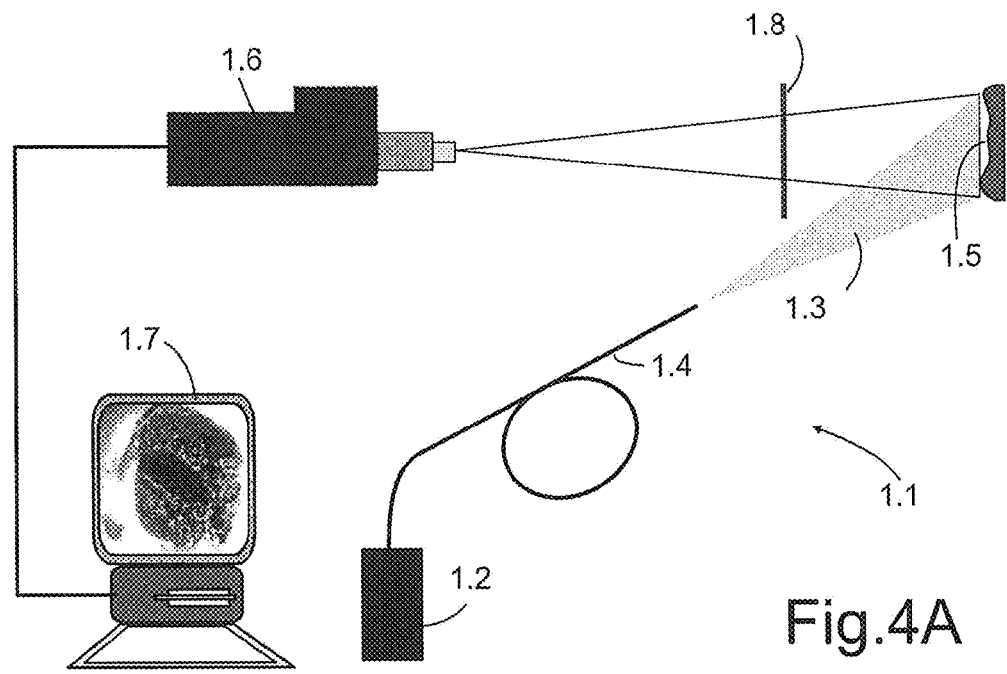

FIG. 4A shows a measuring arrangement 1.1 for taking images of objects to be measured in the light of their fluorescence excited with one-photon excitation. The excitation laser 1.2 emits pulses 1.3 of laser light having a wavelength of, for example, 337 nm, at a pulse length of 2.5 ns. The pulses 1.3 are guided unfocussed through a bundle of optical waveguides 1.4 onto a measuring region 1.5 having a diameter of, for instance, 1 cm. The fluorescence light created by the pulses 1.3 is then passed through a filter 1.8 to an imaging camera 1.6, where it is converted into a grayscale or color-coded image that is proportional to the intensities of the imaged wavelengths. The image is depicted on an evaluation unit 1.7, stored and kept ready for further processing. The images thus taken can be used to scan, for example, larger skin regions for a preliminary assessment of the regions suspected of having a malignant melanoma. According to the unambiguous evaluation criteria cited in the description and shown in FIGS. 1 to 3, this is a purely technical measuring method that can be carried out by a trained technician or, in the future, even by an appropriately configured program, and it yields completely objective results.

Figure 4B:
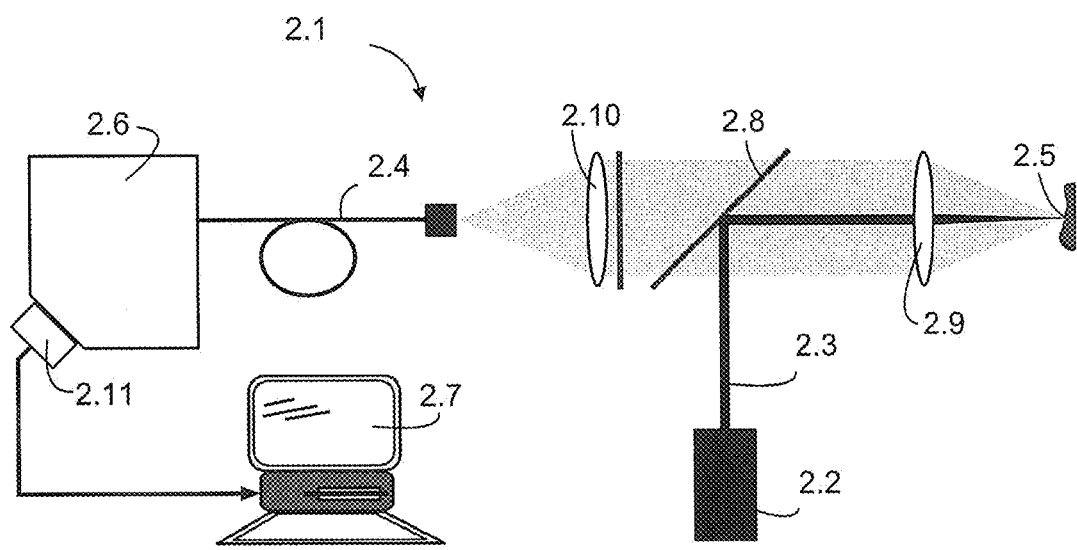

FIG. 4B shows a measuring arrangement 2.1 for the imaging and processing of the fluorescence spectra using two-photon excitation. The excitation laser 2.2 that can be tuned in the wavelength range between 600 nm and 1000 nm emits pulses 2.3 of laser light at a wavelength of, for example, about 850 nm at a pulse length in the range from 0.7 ns to 2.5 ns. The pulses 2.3 are deflected by a dielectric mirror 2.8 that functions as a mirror for certain wavelengths and that is permeable for other wavelengths, and said pulses are focused by a lens system 2.9 onto the measuring spot 2.5 having a diameter, for example, of 70 μm. Consequently, in the measuring spot 2.5, the melanin fraction in the fluorophore mixture—selectively and spatially resolved—is excited to fluorescence. The emitted fluorescence spectrum in the wavelength range between 400 nm and 700 nm is then guided through the lens system 2.9 back to the dielectric mirror 2.8, allowed to pass through the latter and focused by another lens system with a filter 2.10 onto the input of a bundle of optical waveguides 2.4. The bundle 2.4 guides the fluorescence light into a spectrometer 2.6 in which the acquired fluorescence spectrum is resolved and the intensity of the wavelengths is detected in increments of, for example, 25 nm. A secondary electron multiplier 2.11 amplifies the measured result and subsequently feeds it into an evaluation unit 2.7, which depicts it, stores it and keeps it ready for further processing. With the fluorescence spectra thus acquired, for example, measuring spots from the suspicious regions ascertained with the measuring arrangement shown in FIG. 4A can be tested concretely and objectively for the presence of skin regions diseased with the malignant melanoma. Here, too, according to the unambiguous evaluation criteria cited in the description and shown in FIGS. 1 to 3, this is a purely technical measuring method that can be carried out by a trained technician or by a program. It yields completely objective results that can be evaluated by computers. Therefore, the measuring methods described are in their entirety of a purely technical nature and are fundamentally subject to clear and objective evaluation standards employed by trained operating personnel.

The invention claimed is:

1. A method of obtaining a spatially resolved measurement for detection of melanin in a fluorophore mixture of a solid sample, the method comprising:

emitting at least one pulse of light from a laser light source onto the solid sample so as to provide fluorescence excitation of the melanin by photon absorption, wherein the at least one pulse of light has a photon flux density between $10^{26}$ to $10^{28}$ photons per $cm^2$ per second, a pulse length between 0.5 ns and 5 and an excitation wavelength between 300 nm and 1000 nm; and providing an emitted spectral fluorescence response of the melanin by evaluating a number of photons emitted at fluorescence wavelengths between 400 nm and 700 nm so as to identify the melanin.

2. The method as recited in claim 1, wherein the pulse length is 2 ns and the photon flux density is $10^{27}$ photons per $cm^2$ per second.

3. The method as recited in claim 1, wherein the evaluating includes averaging the amount of photons emitted over an accumulation number between 2 and 100 pulses of the laser light source.

4. The method as recited in claim 1, wherein the emitted spectral fluorescence response is provided at wavelength increments of about 25 nm.

5. The method as recited in claim 1, wherein the solid sample has an area of about 1 $cm^2$.

6. The method as recited in claim 1, further comprising the step of:

visually depicting the fluorescence response over the entirety of the solid sample, wherein the excitation wavelength is between 300 nm and 350 nm and the fluorescence excitation is by one-photon absorption.

7. The method as recited in claim 6, wherein the excitation wavelength is about 337 nm.

8. The method as recited in claim 6, wherein the visually depicting step is performed using direct optical photography of the fluorescence response in the range of visible light.

9. The method as recited in claim 6, further comprising the step of:

selecting at least one region of the solid sample having a fluorescence extinction in the depicted fluorescence response, wherein the providing includes ascertaining a fluorescence response at the at least one selected region and at fluorescence wavelengths of about 475 nm and about 575 nm, characteristic of eumelanin and pheomelanin respectively, wherein the excitation wavelength is between 600 nm and 1000 nm and the fluorescence excitation is by stepwise two-photon absorption and the evaluating includes identifying an occurring fraction of pheomelanin by an amount of emitted photons appertaining thereto.

10. The method as recited in claim 9, wherein the fluorescence extinction is determined by at least one of color and grayscale gradations occurring proportionally to a degree of fluorescence extinction and wherein the at least one selected region corresponds to a relatively dark area.

11. The method as recited in claim 9, wherein the evaluating includes identifying an occurring fraction of eumelanin by an amount of emitted photons appertaining thereto and obtaining a ratio of the occurring fractions of eumelanin and pheomelanin.

12. The method as recited in claim 1, wherein the providing includes ascertaining a fluorescence response locally and selectively at fluorescence wavelengths of about 475 nm and about 575 nm, characteristic of eumelanin and pheomelanin respectively, wherein the excitation wavelength is between 600 nm and 1000 nm and the fluorescence excitation is by stepwise two-photon absorption.

13. The method as recited in claim 12, wherein the excitation wavelength is between 800 nm and 900 nm.

14. The method as recited in claim 12, wherein the ascertaining step is performed with a local spatial resolution provided at measuring spots between 40 μm and 100 μm in size.

15. The method as recited in claim 1, wherein the solid sample includes at least one of a tissue-containing portion of human skin, a portion of the fundus of a human eye, and a human hair.

16. The method as recited in claim 15, wherein the solid sample is a freshly biopsied ex-vivo sample.

17. The method as recited in claim 15, wherein the solid sample is stabilized in paraffin and fixed in formalin.

18. The method as recited in claim 15, wherein the solid sample is in-vivo and fixed in a natural environment thereof.

19. The method as recited in claim 1, wherein the solid sample includes human skin tissue and the evaluating is performed so as to identify a malignant melanoma therein.

20. The method as recited in claim 1, wherein the fluorescence excitation is performed substantially exclusive to the melanin.

* * * * *